United States Patent [19]

Fjellestad-Paulsen et al.

[11] Patent Number: 5,922,680
[45] Date of Patent: Jul. 13, 1999

[54] STABILIZED COMPOSITION FOR ORAL ADMINISTRATION OF PEPTIDES

[75] Inventors: Anne Fjellestad-Paulsen, Paris, France; Christina Ahlm-Söderberg, Malmö, Sweden

[73] Assignee: Ferring, B.V., Hoofddorp, Netherlands

[21] Appl. No.: 08/977,975

[22] Filed: Nov. 25, 1997

Related U.S. Application Data

[63] Continuation of application No. 08/676,400, Oct. 23, 1996, Pat. No. 5,763,405.

[51] Int. Cl.⁶ .......................... A61K 38/00; A61K 38/02; C07K 5/00; C07K 7/00
[52] U.S. Cl. .................. 514/15; 514/16; 530/300; 530/315; 530/327; 530/328
[58] Field of Search ................. 514/15, 16; 530/300, 530/315, 327, 328

[56] References Cited

U.S. PATENT DOCUMENTS

| | | |
|---|---|---|
| 3,497,491 | 2/1970 | Zaoral et al. . |
| 3,794,633 | 2/1974 | Kamber et al. . |
| 3,929,758 | 12/1975 | Hughes et al. . |
| 4,033,940 | 7/1977 | Hughes et al. . |
| 4,093,610 | 6/1978 | Abraham et al. . |
| 4,216,141 | 8/1980 | Rivier et al. . |
| 4,271,068 | 6/1981 | Kamber et al. . |
| 4,351,764 | 9/1982 | Birr . |
| 4,487,765 | 12/1984 | de Wied . |
| 5,047,398 | 9/1991 | Hagstam et al. . |
| 5,066,716 | 11/1991 | Robey et al. . |
| 5,482,931 | 1/1996 | Harris et al. . |
| 5,498,598 | 3/1996 | Harris . |
| 5,500,413 | 3/1996 | Larsson et al. . |
| 5,596,078 | 1/1997 | Andersson et al. . |
| 5,674,850 | 10/1997 | Larsson et al. . |
| 5,763,405 | 6/1998 | Fjellestad-Paulsen et al. .......... 514/15 |

*Primary Examiner*—Avis M. Davenport
*Attorney, Agent, or Firm*—Hopgood, Calimafde Kalil & Judlowe

[57] ABSTRACT

A solid pharmaceutical composition for oral administration of small and medium size peptides, particularly vasopressin, oxytocin, and their analogues, comprises said peptide, an enteric coat and a pharmaceutically acceptable carrier containing a buffering agent buffering at a pH of from 2 to 6, preferably at about pH 5. A method of manufacture of single doses of said peptide comprises mixing of the ingredients, forming the resulting mixture into spheres smaller than 2 mm, coating the spheres with an enteric coat which is readily soluble in gastric juice of pH 5.0 or higher but not at substantially lower pH, and filling the coated spheres in capsules or incorporating them into tablets, degradable in the stomach. Also disclosed is a method for oral administration to a patient of said single dose.

4 Claims, 2 Drawing Sheets

DDAVP uptake in small intestine of male rats; citrate buffer, pH 2.5 at start

DDAVP uptake in small intestine of male rats; 0.9 % NaCl ing of carbohydrates and modified carbohydrates and derivatives thereof, polyethylene and/or polypropylene glycol and derivatives thereof, inorganic fillers or lubricating agents, fatty acids and their esters and salts, preservatives and coating agents. Suitable pharmaceutical acceptable carriers comprise a wide variety of carriers for production of pharmaceutical formulations in tablet or capsule form, e.g. the carrier of the antidiuretic composition containing DDAVP disclosed in the European patent no. 163 723. Especially preferred are multiparticle systems, such as systems for administration in soft and hard gelatin capsules; preferred particle sizes for spheres containing peptide and/or protease inhibitor are below about 2 mm.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 5 amino acids
      (B) TYPE: amino acid
      (C) TOPOLOGY: linear (ii) MOLECULE TYPE: peptide (xi) SEQUENCE DESCRIPTION: SEQ ID NO:1:

Ile Thr Asn Cys Pro
      1          5

(2) INFORMATION FOR SEQ ID NO:2:

(i) SEQUENCE CHARACTERISTICS:
      (A) LENGTH: 7 amino acids
      (B) TYPE: amino acid
      (C) TOPOLOGY: linear (ii) MOLECULE TYPE: peptide (xi) SEQUENCE DESCRIPTION: SEQ ID NO:2:

Ile Gln Asn Cys Pro Leu Gly
      1          5

(2) INFORMATION FOR SEQ ID NO:3:

(i) SEQUENCE CHARACTERISTICS:
      (A) LENGTH: 6 amino acids
      (B) TYPE: amino acid
      (C) TOPOLOGY: linear (ii) MOLECULE TYPE: peptide (xi) SEQUENCE DESCRIPTION: SEQ ID NO:3:

Tyr Phe Gln Asn Cys Pro
      1          5

(2) INFORMATION FOR SEQ ID NO:4:

(i) SEQUENCE CHARACTERISTICS:
      (A) LENGTH: 8 amino acids
      (B) TYPE: amino acid
      (C) TOPOLOGY: linear (ii) MOLECULE TYPE: peptide (xi) SEQUENCE DESCRIPTION: SEQ ID NO:4:

```
Cys Tyr Ile Asn Cys Pro Leu Gly
 1               5
```

STABILIZED COMPOSITION FOR ORAL ADMINISTRATION OF PEPTIDES This application is a continuation of application Ser. No. 08/676,400 filed Oct. 23, 1996 now U.S. Pat. No. 5,763,405.

The present invention relates to pharmaceutical compositions in solid form for oral administration of small and medium size peptides, particularly vasopressin, oxytocin, and their analogues. The present invention also relates to a method for manufacture of a single dose of said composition for oral administration of small and medium-size peptides, particularly vasopressin, oxytocin, and their analogues.

The invention further relates to a method for administration of said composition to a patient.

BACKGROUND

A number of medicines for treatment of a variety of diseases contain, as active principle, naturally occurring peptides or their synthetic analogues.

Because of the instability of small and medium size peptides, particularly vasopressin, oxytocin, and their analogues, in the environment of the gastrointestinal tract their uptake, when given as a medicine or for similar reasons, is still very unsatisfactory. Thus, better delivery systems for non-parenteral, particularly for oral, administration of peptides and their analogues are desirable, cf. Davies, S.: "Developing delivery systems for peptides and proteins", *Scrip Magazine* 1992, 34–38.

OBJECTS OF THE INVENTION

It is an object of the present invention to provide a pharmaceutical composition of the kind known in the art and mentioned above which provides for better absorption of said small or medium-size peptides, particularly vasopressin, oxytocin, and their analogues.

It is another object of the present invention to provide a method of manufacture of a single dose of said pharmaceutical composition for oral administration of small and medium-size peptides, particularly vasopressin, oxytocin, and their analogues.

It is a further object of the invention to provide a method for administration of said composition to a patient.

Additional objects of the present invention will become evident by study of the detailed description of preferred embodiments of the invention.

SUMMARY OF THE INVENTION

The above and other objects of the invention are provided by a pharmaceutical composition of the kind described above, said composition comprising a small and medium size peptide, particularly vasopressin, oxytocin, or an analog of vasopressin or oxytocin, an enteric coat, and a pharmaceutically acceptable carrier containing a buffering agent buffering at a pH of from 2 to 6, more preferred from 4 to 5,5, most preferred at about pH 5. It is preferred for the peptide to be chosen from DDAVP (desmopressin), oxytocin, CAP (atosiban), and carbetocin. Particularly preferred is DDAVP. For full sequences of these peptides, see Table 1 at the end of the DETAILED DESCPRIPTION section. Another group of peptides preferred for oral administration by incorporation into the composition according to the invention comprises GnRH-analogues (gonadotropin-releasing hormone analogues) such as gonadorelin and triptorelin.

It is preferred for the the pharmaceutically acceptable carrier to further comprise one or several agents selected from the group consisting of carbohydrates and modified carbohydrates and derivatives thereof, polyethylene and/or polypropylene glycol and derivatives thereof, inorganic fillers or lubricating agents, fatty acids and their esters and salts, preservatives and coating agents. Suitable pharmaceutical acceptable carriers comprise a wide variety of carriers for production of pharmaceutical formulations in tablet or capsule form, e.g. the carrier of the antidiuretic composition containing DDAVP disclosed in the European patent no. 163 723. Especially preferred are multiparticle systems, such as systems for administration in soft and hard gelatin capsules; preferred particle sizes for spheres containing peptide and/or protease inhibitor are below about 2 mm.

According to a preferred aspect of the invention the enteric coat is designed for release of its contents in the small intestine. It is particularly preferred for the particles contained in the tablets or capsules to be coated with an enteric coating for delayed release of their contents in the upper part of the small intestine. Especially preferred is delayed release of the peptide and the protease inhibitor in the duodenum and the jejunum, particularly in the duodenum and the upper jejunum. The enteric-coated spheres may also be contained in a tablet that readily disintegrates in the stomach or may be administered in suspended form in media that will not readily dissolve the enteric coating. It is also possible for the peptide and the protease inhibitor to be contained in separate spheres having the same type of enteric coating.

It is preferred for the enteric coat to be soluble in gastric juice at a pH of about 5.0 or higher; particularly preferred is a pH of about 5.5 or higher. Enteric coatings that are not readily dissolvable in such fluids at a pH of about 6.5, however, will not permit substantial release of the ingredients of the composition according to the invention in the upper small intestine and, therefore, are not preferred; on the other hand, coatings that dissolve in gastric fluids at a pH substantially lower than 5,0 are less preferred since they will release the ingredients in the stomach. Useful enteric coatings according to the invention comprise polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers, as well as polyvinylacetate phthalates and similar partial esters of dibasic or tribasic carboxylic acids with polyvinylacetate and similar polymers carrying alcoholic hydroxyl groups. The enteric coating may also advantageously be prepared from mixtures of such polymers.

The peptide and/or the protease inhibitor is preferably admixed with a carrier comprising a buffering agent and one or several agents selected from the group consisting of carbohydrates and modified carbohydrates and derivatives thereof, polyethylene and/or polypropylene glycol and derivatives thereof, organic and inorganic core, filler or lubricating materials, fatty acids, their esters and salts, preservatives, antioxidants, and coating agents. The buffering agent should be able to buffer at a pH from about 2 to about 6, more preferred from about 4 to 5,5, most preferred at about pH 5, i.e. to exert substantial buffer capacity within this range and preferably at about pH 5. A pH lower than about 2 can also be used but is not preferred because of risk of injury of the intestinal wall in long term use. The preferred pH-range according to the invention is a compromise between, at the one hand, maximizing stabilization effect and, on the other hand, protection of the intestinal wall against potential injury by low pH. Since the composition according to the invention is intended for preferred release in the upper part of the small intestine where, during their passage, the acidic contents of the stomach are neutralized by influx of $Na^+$, buffering inhibits or delays an increase of pH exceeding the preferred range or, in other words, in the direction of the upper limit of the preferred range and exceeding that upper limit. The buffering agent thus forms a barrier for the natural neutralization of the stomach's content upon emptying into the small intestine through the pylorus. Preferred buffering agents are hydrogen and dihydrogen phosphates, such as sodium dihydrogen phosphate and mixtures of sodium dihydrogen phosphate with disodium hydrogen phosphate, calcium tetrahydrogen phosphate, citric acid and mixtures of citric acid and its monosodium salt, fumaric acid and its monosodium salt, adipic acid and its monosodium salt, tartaric acid and its sodium salt, ascorbic acid and its monosodium salt, glutamic acid, aspartic acid, betaine hydrochloride, hydrochlorides of amino acids, such as arginine monohydrochloride and glutamic acid hydrochloride, and saccharic acid. It is preferred for the buffering agent to comprise at least 10% by weight, more preferred at least 25% by weight, most preferred at least 40% by weight of the composition according to the invention. A mixture of two or more buffering constituents can be used.

According to the invention there is also provided a method of manufacture of single doses of the composition according to the invention, said method comprising the following steps:

mixing the peptide and a suitable carrier including a buffering agent buffering in the range from pH 2 to pH 6, more preferred from pH 4 to pH 5,5, most preferred at about pH 5, spheronizing the mixture for formation of spheres with a diameter smaller than about 2 mm, coating the spheres with an enteric coat which is readily soluble in gastric juice of pH 5.0 or higher but not readily soluble at substantially lower pH, filling the coated spheres in capsules or incorporating them into tablets, said capsules or tablets being readily disintegrable in the stomach.

The invention further relates to a method for administration of a single dose of a small and medium-size peptide, particularly vasopressin, oxytocin, and their analogues, to a patient, comprising administering orally to the patient a tablet or capsule containing a pharmacologically effective amount of said small and medium-size peptide in form of the composition according to the invention, said tablet or capsule being disintegrable in the stomach.

DETAILED DESCRIPTION

Figure 1:
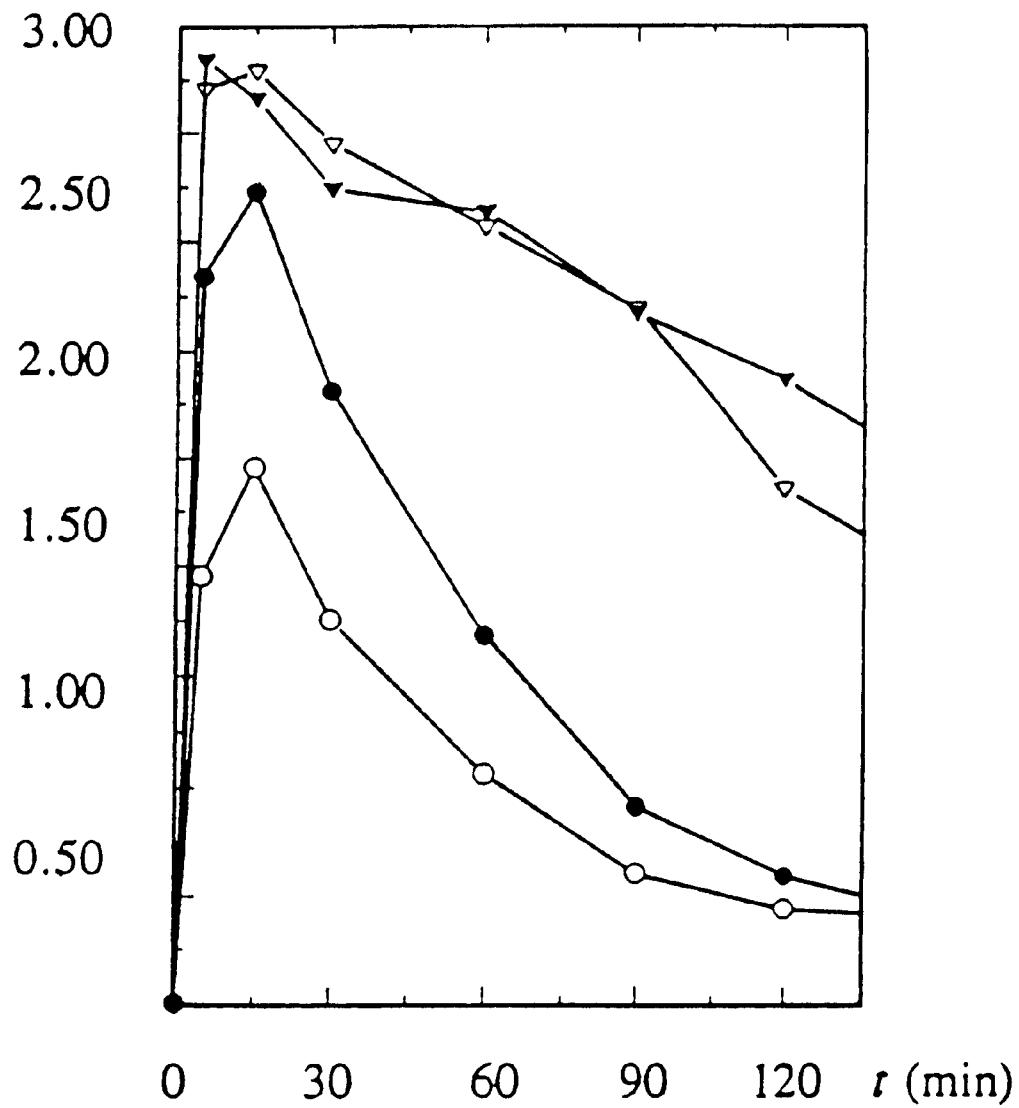

The invention will now be described in greater detail by reference to degradation of DDAVP in gastric juice.

EXAMPLE 1

Human gastro-intestinal juice was obtained from healthy male volunteers who had been fasting for 8 h. A tube was introduced intranasally after local anaesthesia with xylocaine, and gastric juice was collected. Thereafter one standardized meal was given 1 h before sampling of duodenal and distal jejunum juice and another the next morning before the collection of distal ileal juice. After centrifugation the gastric and intestinal juices were frozen in aliquots of 1 ml and stored at $-20°$ C.

Degradation method. The peptide or peptide analog (10 $\mu$l of 10 mM peptide in 0.9% aqueous NaCl) was added to 190 $\mu$l of undiluted juice at $37°$ C. Aliquots of 25 $\mu$l were withdrawn at intervals and mixed with 100 $\mu$l acetone to stop the reaction. After centrifugation for 10 min at 10,000 g, 10 $\mu$l of the supernatant was analyzed by reversed phase HPLC.

Determination of peptide degradation. Analysis was carried out in a Varian 5000 HPLC analyzer equipped with a UV-detector (220 nm). Column Bondapak TM C18 (3.9× 300 mm), eluant MeOH/0.025 M $NH_4Ac$ (isocratic conditions), flow rate 1 ml/min.

Protein and pH determination. Protein: Bio-Rad protein assay. pH: Orion model SA720; pH-paper Merck (Darmstadt), range 4.0–7.0.

Results. DDAVP was found to be degraded (to about 50% after 35 min) by both gastric and intestinal juices at pH 6.5. When the pH was adjusted to 4.0 DDAVP appeared to be essentially stable. Absent pH-adjustment, DDAVP proteolysis was found to be slower in jejunal or duodenal juice than in ileal juice.

EXAMPLE 2

Experiments in rat.

Figure 2:
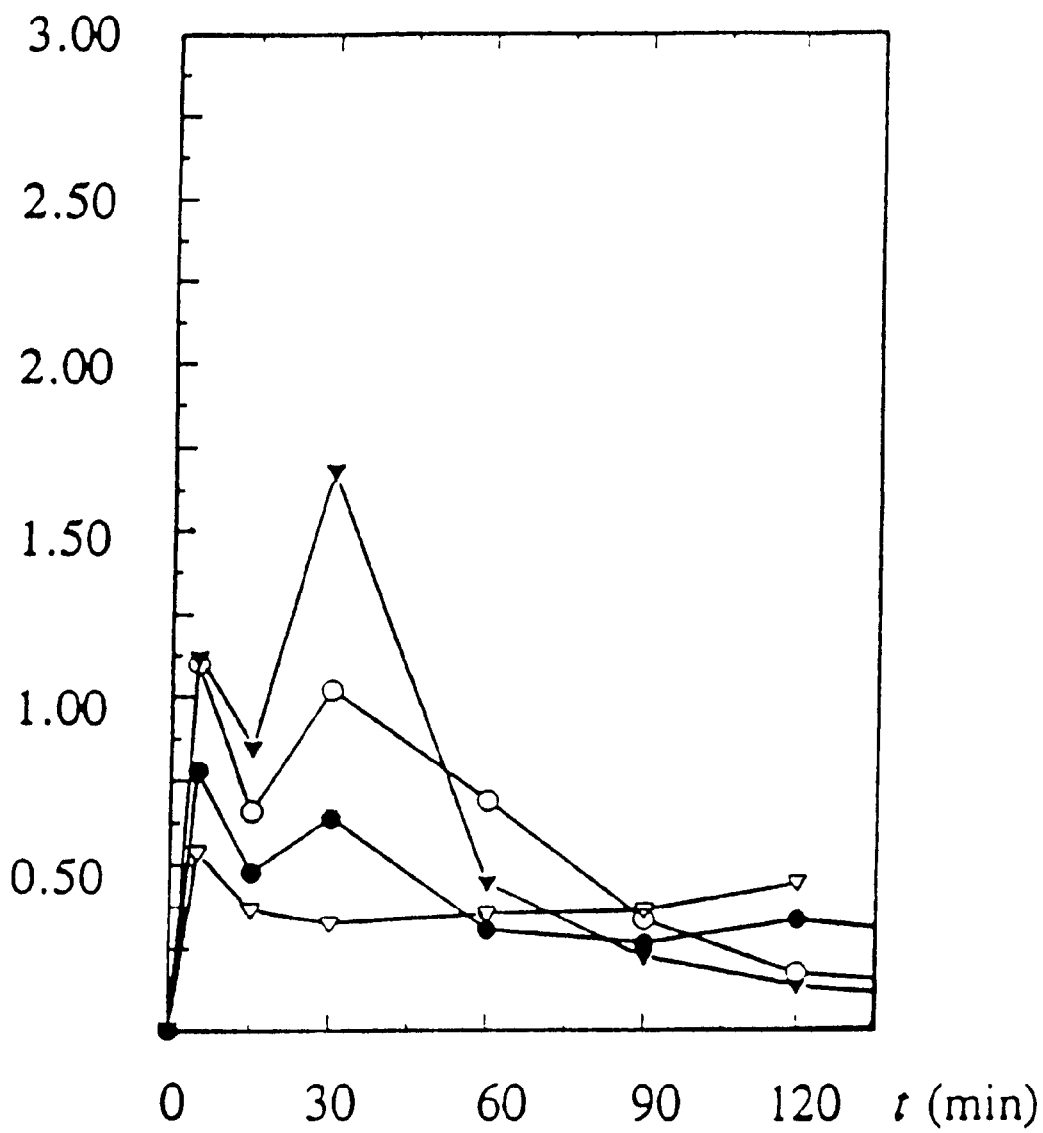

SPD male rats weighing about 300 g were anaesthetized with 15 mg/kg with thiobutabarbital sodium (Inactinp198, Byk Gulden, Germany). After opening the abdominal cavity a cut about 3 mm in length was made in the small intestine about 15 mm distally from the pylorus. Through this cut a gelatin capsule was inserted into the small intestine, the capsule containing 0:10 ml of peptide solution containing 2.0 mg peptide per ml of aqueous citrate buffer solution (pH about 2,5, prepared by mixing 22.3 ml of 1 M citric acid, 2,7 ml of 2.0 M sodium phosphate and 25 ml of water). Time record was started, the intestine sutured and the abdominal cavity closed. Blood samples were drawn at predetermined intervals from a catheter in the carotid artery. Peptide content determination was by RIA. Results shown in FIG. 1 demonstrate the stabilizing effect of the composition according to the invention over the corresponding non-buffered preparation (FIG. 2) which was prepared by dissolving a corresponding amount of DDAVP in 0.9% of saline. The results for the four rats used in each experiment are shown in separate curves.

EXAMPLE 3

Tablets according to the invention containing selected amounts of DDAVP and a pH-buffering agent (25% by weight of calcium tetrahydrogen phosphate and 3% by weight of disodium hydrogen phosphate) can be manufactured by slight modification (addition of aprotinin) of the method disclosed in EP-A-0 163 723. These tablets can be spray-coated with useful enteric coatings such as described by Agyilirah, G. A. and Banker, G. S. in Polymers for controlled drug delivery, Tarcha, P. J., Ed., CRC Press, Boca Raton 1991, p. 39–66.

EXAMPLE 4

Hard gelatin capsules containing a particulate enteric-coated DDAVP formulation according to the invention can be obtained in the following way. Solid core particles (100 g) prepared according to EP-A2-0 366 722 (example 3) are coated with 760 ml of an aqueous solution containing 20.0 mg DDAVP acetate, and these coated particles are spray-coated in a Spheronizer® fluid-bed coater with a methanol—methylene chloride 1:1 coating solution containing (by weight) 10% of polyvinyl acetate phthalate (PVAP; TD-17, Colorcon Inc., West Point, Pa.), 0.7 of glyceryl triacetate and 1% of stearic acid, and dried. Hard gelatin capsules are filled with these enteric-coated particles (250 mg/capsule).

TABLE 1

| Peptide or peptide analog | Sequence | |
|---|---|---|
| CAP (atosiban) | Mpa-D-Tyr(Et)-Ile-Thr-Asn-Cys-Pro-Orn-GlyNH$_2$ | (SEQ ID NO:1) |
| carbetocin | Bua-Tyr(Me)-Ile-Gln-Asn-Cys-Pro-Leu-GlyNH$_2$ | (SEQ ID NO:2) |
| DDAVP (desmopressin) | Mpa-Tyr-Phe-Gln-Asn-Cys-Pro-D-Arg-Gly-GlyNH$_2$ | (SEQ ID NO:3) |
| oxytocin | Cys-Tyr-Ile-Asn-Cys-Pro-Leu-GlyNH$_2$ | (SEQ ID NO:4) |

We claim:

1. An oral pharmaceutical composition in solid form comprising desmopressin, an enteric coat soluble in gastric juices at and above a pH of about 5.5, but not readily soluble at a pH lower than 5.0, said coat selected from polymers having dissociable carboxyl groups, and a pharmaceutically acceptable carrier containing a buffering agent buffering at a pH of from 2 to 6.

2. The composition according to claim 1, wherein said pharmaceutically acceptable carrier further comprises an agent selected from the group consisting of carbohydrates, modified carbohydrates, polyethylene glycol, polypropylene glycol, inorganic fillers, lubricating agents, fatty acids, preservatives and coating agents.

3. The composition according to claim 1, wherein said enteric coat releases its contents in the upper part of the small intestine.

4. The composition according to claim 1, wherein said enteric coat is selected from the group consisting of hydroxypropyl methyl cellulose phthalate, cellulose acetate phthalate, cellulose acetate trimellitate, phthalates of vinyl acetate, tribasic carboxylic acids with polyvinyl acetate and polymers carrying alcoholic hydroxyl groups.

* * * * *